US009506025B2

(12) United States Patent
Yoo et al.

(10) Patent No.: US 9,506,025 B2
(45) Date of Patent: Nov. 29, 2016

(54) CULTURED MUSCLE PRODUCED BY MECHANICAL CONDITIONING

(75) Inventors: James Yoo, Winston-Salem, NC (US); Joel Stitzel, Winston Salem, NC (US); Anthony Atala, Winston-Salem, NC (US); George Christ, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 130 days.

(21) Appl. No.: 12/429,385

(22) Filed: Apr. 24, 2009

(65) Prior Publication Data

US 2009/0265005 A1 Oct. 22, 2009

Related U.S. Application Data

(62) Division of application No. 11/279,671, filed on Apr. 13, 2006.

(60) Provisional application No. 60/671,600, filed on Apr. 15, 2005.

(51) Int. Cl.
*A61F 2/08* (2006.01)
*C12M 1/42* (2006.01)
*A61L 27/38* (2006.01)
*C12M 3/00* (2006.01)
*C12N 5/077* (2010.01)

(52) U.S. Cl.
CPC .......... *C12M 35/04* (2013.01); *A61L 27/3826* (2013.01); *A61L 27/3895* (2013.01); *C12M 21/08* (2013.01); *C12N 5/0658* (2013.01)

(58) Field of Classification Search
CPC . C12M 35/02; C12M 21/08; A61L 27/3895; C12N 5/0658; A01B 12/006
See application file for complete search history.

(56) References Cited

U.S. PATENT DOCUMENTS

| | | |
|---|---|---|
| 4,839,280 A | 6/1989 | Banes |
| 4,910,138 A | 3/1990 | Miura |
| 4,940,853 A | 7/1990 | Vandenburgh |
| 5,336,616 A | 8/1994 | Livesey et al. |
| 5,348,879 A | 9/1994 | Shapiro |
| 5,406,853 A | 4/1995 | Lintilhac et al. |
| 5,695,996 A | 12/1997 | Quinn et al. |
| 5,750,329 A | 5/1998 | Quinn et al. |
| 5,773,285 A | 6/1998 | Park |
| 5,795,710 A | 8/1998 | Park |
| 5,858,783 A | 1/1999 | Goodwin et al. |
| 6,051,750 A | 4/2000 | Bell |
| 6,057,150 A | 5/2000 | Lee et al. |
| 6,107,081 A | 8/2000 | Feeback et al. |
| 6,162,642 A | 12/2000 | Redbrake-Adams et al. |
| 6,376,244 B1 | 4/2002 | Atala |
| 6,472,202 B1 | 10/2002 | Banes |
| 6,479,064 B1 | 11/2002 | Atala |
| 6,576,457 B1 | 6/2003 | Hua |
| 6,592,623 B1 | 7/2003 | Bowlin et al. |
| 6,645,759 B2 | 11/2003 | Banes |
| 6,743,435 B2 | 6/2004 | De Vore et al. |
| 6,962,814 B2 | 11/2005 | Mitchell et al. |
| 7,563,280 B2 | 7/2009 | Anderson et al. |
| 7,604,663 B1 | 10/2009 | Reimink et al. |
| 2002/0115208 A1* | 8/2002 | Mitchell et al. ............ 435/325 |
| 2005/0013870 A1 | 1/2005 | Freyman et al. |
| 2005/0028228 A1* | 2/2005 | McQuillan et al. .......... 800/17 |
| 2005/0260612 A1* | 11/2005 | Padmini et al. ............... 435/6 |
| 2008/0195229 A1 | 8/2008 | Quijano et al. |

FOREIGN PATENT DOCUMENTS

| | | | |
|---|---|---|---|
| WO | WO 00/34442 | | 6/2000 |
| WO | WO 01/49827 | * | 7/2001 |
| WO | WO0240630 A2 | * | 5/2002 |

OTHER PUBLICATIONS

Powell et al. "Mechanical stimulation improves tissue-engineered human skeletal muscle." American Journal of Physiology—Cell Physiology (2002);283: pp. C1557-C1565.*
International Search Report and Written Opinion for PCT/US06/13963; Date of mailing Nov. 29, 2006.
Moon SG et al. Cyclic mechanical preconditioning improves engineered muscle contraction. Tissue Engineering: Part A. 2008; 14(4): 473-482.
Vandenburgh H and Kaufman S. In vitro model for stretch-induced hypertrophy of skeletal muscle. Science. Jan. 19, 1979; 203: 265-268.
Clarke MSF and Feeback DL. Mechanical load induces sarcoplasmic wounding and FGF release in differentiated human skeletal muscle cultures. FASEB J. 1996; 10: 502-509.
Tatsumi R et al. Mechanical stretch induces activation of skeletal muscle satellite cells in vitro. Experimental Cell Research. 2001; 206: 107-114.
Waters CM et al. A system to impose prescribed homogenous strains on cultured cells. J. Appl. Physiol. 2001; 91: 1600-1610.
Dahms SE et al. Compositions and biomechanical properties of the bladder acellular matrix graft: comparative analysis in rat, pig and human. British Journal of Urology. 1998; 82: 411-419.
Vandenburgh HH. A computerized mechanical cell stimulator for tissue culture: effects on skeletal muscle organogenesis. In Vitro Cellular & Developmental Biology. Jul. 1988; 24(7): 609-619.

(Continued)

*Primary Examiner* — Titilayo Moloye
(74) *Attorney, Agent, or Firm* — Myers Bigel, P.A.

(57) ABSTRACT

A method of producing organized skeletal muscle tissue from precursor muscle cells in vitro comprises: (a) providing precursor muscle cells on a support in a tissue media; then (b) cyclically stretching and relaxing the support at least twice along a first axis during a first time period; and then (c) optionally but preferably maintaining the support in a substantially static position during a second time period; and then (d) repeating steps (b) and (c) for a number of times sufficient to enhance the functionality of the tissue formed on the support and/or produce organized skeletal muscle tissue on the solid support from the precursor muscle cells.

15 Claims, 7 Drawing Sheets

(56) References Cited

OTHER PUBLICATIONS

Stegeman JP and Nerem RM. Phenotype modulation in vascular tissue engineering using biochemical and mechanical stimulation. Annals of Biomedical Engineering. 2003; 31(4): 391-402.
Supplementary European Search Report, EP 06750099, Apr. 21, 2009.
European Examination Report, EP 06750099, mailed Jul. 31, 2009.
Grinnell F et al. Dendritic fibroblasts in three-dimensional collagen matrices. Molecular Biology of the Cell. Feb. 2003; 14: 384-395.
Quinn A. U.S. military develops implantable muscles. Smart Planet. Jul. 16, 2012: 1 pp.
Science Daily. Lab-engineered muscle implants restore function in animals. Jul. 2012: 3 pp.
Corona BT et al. Further development of a tissue engineered muscle repair construct in vitro for enhanced functional recovery following implantation in vivo in a murine model of volumetric muscle loss injury. Tissue Engineering: Part A. 2012; 18(11-12): 1213-1228.
Corona BT et al. Implantation of in vitro tissue engineered muscle repair constructs and bladder acellular matrices partially restore in vivo skeletal muscle function in a rat model of volumetric muscle loss injury. Tissue Engineering: Part A. 2014. 20, Nos. 3 and 4, 705-715.
Decision on Appeal, corresponding to U.S. Appl. No. 11/279,671, Mailed Jul. 21, 2015, 9 pages.
Machingal, M., et al. "A Tissue-Engineered Muscle Repair Construct for Functional Restoration of an Irrecoverable Muscle Injury in a Murine Model", *Tissue Engineering Part A*, vol. 17, 2011, pp. 2291-2303.
Morgan JE and Partridge TA. Muscle satellite cells. International Journal of Biochemistry & Cell Biology. Aug. 2003; 35(8): 1151-1156.

\* cited by examiner

2 WEEK TETANUS TEST; 50 v

4 WEEK TETANUS TEST; 50 v

NORMAL BACK MUSCLE TEST; 50 v

CULTURED MUSCLE PRODUCED BY MECHANICAL CONDITIONING

RELATED APPLICATIONS

This application claims priority to and is a divisional of U.S. patent application Ser. No. 11/279,671, filed Apr. 13, 2006, and also claims the benefit of U.S. Provisional Patent Application Ser. No. 60/671,600, filed Apr. 15, 2005, the disclosure of each of which is incorporated by reference herein in its entirety.

FIELD OF THE INVENTION

The present invention concerns methods and apparatus for the growth of skeletal muscle in vitro.

BACKGROUND OF THE INVENTION

Loss of functional skeletal muscle due to traumatic injury, tumor excision, etc., produces a physiological deficit for which there is still no effective clinical treatment. Tissue engineering of skeletal muscle in vitro for functional tissue replacement in vivo may provide a potential therapeutic solution to this unmet medical need. In fact, significant progress has been made during last 15 years in understanding some of the basic requirements for creating tissue engineered skeletal muscle constructs in vitro. Early studies necessarily focused mainly on the production of highly differentiated muscle constructs and characterizing their properties in terms of response to stretch and other mechanical stimulation in a 2-D tissue culture system (Vandenburgh, *Mechanical forces and their second messengers in stimulating cell growth in vitro*. Am J. Physiol. 262(3 Pt 2):R350-5 (March 1992); *Mechanical stimulation of skeletal muscle generates lipid-related second messengers by phospholipase activation*. J Cell Physiol. 155(1):63-71 (April 1993).

The majority of recent work on 3-D cultures of skeletal muscle myoblasts has been performed using gel-based matrix and mechanical strainers; as biodegradable scaffolds are thought to possess too much of a development barrier (both structural and nutritional) to clinical development. Recently, 3-D cultures of myoblasts have been successfully established and isometric contractile responses in these 3-D constructs, termed myoids, were measured (Dennis R G, Kosnik P E. *Excitability and isometric contractile properties of mammalian skeletal muscle constructs engineered in vitro*. In Vitro Cell and Dev Biol Animal. 36:327-335 (2000)). Additionally, fibrin-based gels were suggested as another novel method to engineer 3-D functional muscle tissue. The latter achieved muscle structures of 100-500 μm diameter with measured maximal tetanic force of 805.8±55 μN (Huang Y et al., *Rapid formation of functional muscle in vitro using fibrin gels*. J Appl Physiol 98: 706-713 (2005)). In short, tissue engineered 3-D skeletal muscle constructs composed of collagen or fibrin gels have clearly improved the understanding of skeletal muscle organogenesis and provide a reasonable model for studying the developmental physiology of skeletal muscle micro-structures in vitro.

However, while muscle constructs developed with synthetic scaffolds can support the contractile portion of the muscle tissue, and furthermore, can be maintained in culture for several months, this approach still has significant limitations for clinical utility. For example, implantation of tissue engineered skeletal muscle constructs will require that they be of relevant size and mechanical strength to be amenable to the rigors of the requisite surgical procedures. Clearly, gel-based constructs are currently too small and too fragile for such surgical manipulatation.

As such, one of the major barriers to engineering clinically applicable functional muscle tissues for reconstructive procedures is the lack of a bioreactor system and methodology that would accelerate cellular organization, tissue formation and function.

SUMMARY OF THE INVENTION

A first aspect of the invention is a method of culturing organized skeletal muscle tissue from precursor muscle cells. In general the method comprises: (a) providing precursor muscle cells on a support in a tissue media; then (b) cyclically stretching and relaxing the support at least twice along a first axis during a first time period; and then (c) optionally but preferably maintaining the support in a substantially static position during a second time period; and then (d) repeating steps (b) and (c) for a number of times sufficient to enhance the functionality of the muscle tissue (e.g., its ability to contract), or produce organized skeletal muscle tissue, on the solid support from the precursor muscle cells.

An alternate embodiment of the foregoing includes the step of cyclically stretching and relaxing said support at least twice along a second axis during said first time period (with stretching and relaxing along still additional axes being possible if desired).

A second aspect of the invention is cultured skeletal muscle tissue produced by a process as described herein.

A third aspect of the invention is cultured skeletal muscle tissue. The tissue is characterized by cells that exhibit, or its ability to exhibit, a reproducible contractile response to KCl-induced depolarization in vitro. In some embodiments the tissue is further characterized by a unidirectional orientation on histological examination; the presence of multinucleated myofibril cells; cells that express muscle markers as confirmed by immunohistochemistry (e.g., alpha actin and myosin heavy chain); contains and cells that produce extracellular matrices as confirmed by Mason's Trichrome.

A further aspect of the invention is a device useful for carrying out a method as described herein. The device preferably comprises a container, a pair of engaging members in said container for engaging tissue supports or other tissue constructs, an actuator mounted on the container and operatively associated with one of said engaging members to provide controlled cyclic strain to attached tissue supports or other tissue constructs, a motor connected to said actuator, and a controller operatively associated with said motor. All are positioned so that supports or constructs carried by the engaging members may be immersed in a suitable growth or culture media in the container. The controller is configured to implement a method as described herein. The engaging members preferably include a plurality of points of attachment so that a plurality of tissue supports or tissue constructs, each with its own volume of space within the container, are provided.

The foregoing and other objects and aspects of the present invention are explained in greater detail in the drawings herein and the specification set forth below.

Panel C is normal muscle as a control.

Figure 6:
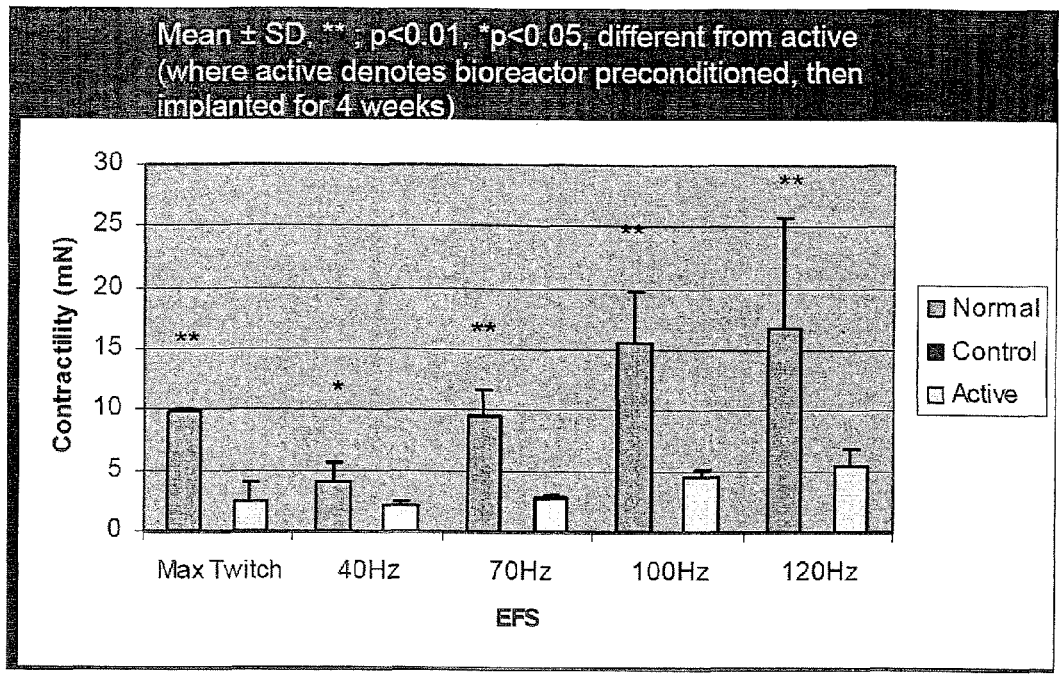

FIG. 6. Graphical summary of the results of physiological experiments performed at the 4 week time point on isolate skeletal muscle tissue strips in vitro.

Figure 7:
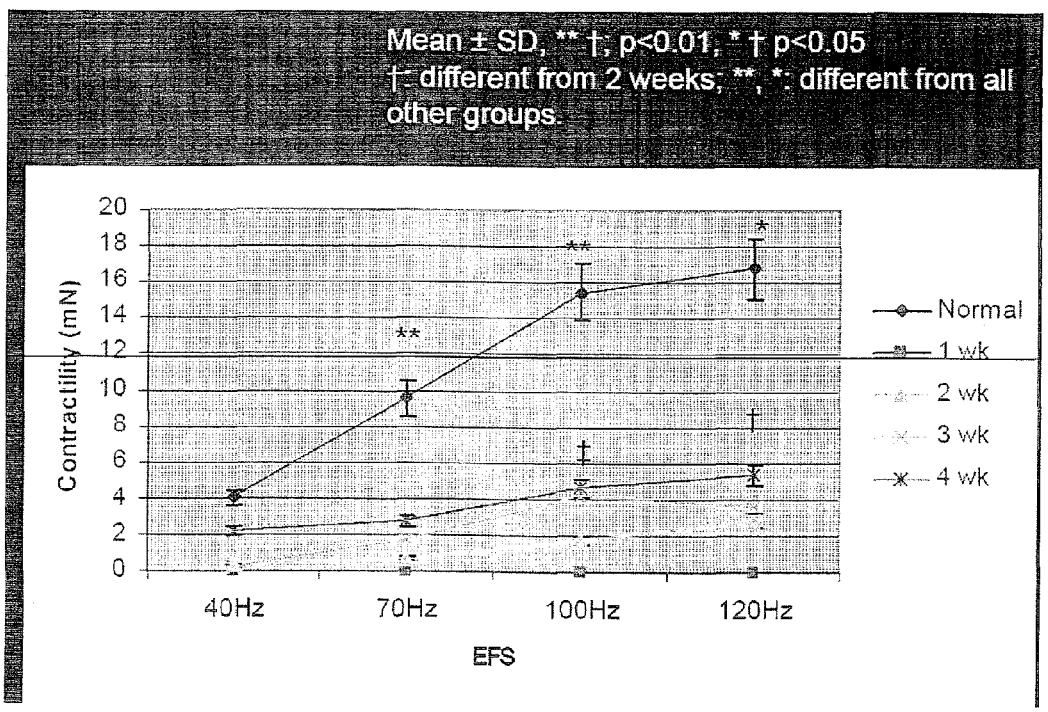

FIG. 7. Graphical summary of the results of all physiological experiments performed on isolate skeletal muscle tissue strips in vitro.

The present invention is explained in greater detail in the drawings herein and the specification below. The disclosures of all United States patent references cited herein are to be incorporated by reference herein in their entirety.

DETAILED DESCRIPTION OF THE PREFERRED EMBODIMENTS

Subjects to be treated by the methods of the present invention include both human subjects and other animal subjects (particularly mammalian subjects such as dogs and cats) for veterinary purposes.

Muscle cells used to carry out the present invention are preferably mammalian muscle cells, including primate muscle cells, including but not limited to human, pig, goat, horse, mouse, rat, monkey, baboon, etc. In general such cells are skeletal muscle cells. Muscle cells of other species, including birds, fish, reptiles, and amphibians, may also be used if so desired. The muscle cells are, in general, precursor cells, or cells that are capable of differentiating into muscle cells, specifically skeletal muscle cells, under appropriate culture conditions and stimuli as described herein. Muscle precursor cells are known. See, e.g., U.S. Pat. No. 6,592,623.

"Supports" on which muscle cells may be seeded and grown to produce cultured muscle tissue of the present invention include any suitable support. See, e.g., U.S. Pat. Nos. 6,998,418; 6,485,723; 6,206,931; 6,051,750; and 5,573,784. Collagen supports or decellularized tissue supports (e.g., obtained from smooth muscle or skeletal muscle, such as a decellularized mammalian (e.g., porcine) bladder, are currently preferred.

Any suitable culture media can be used to grow cells in the present invention, including medias comprising serum and other undefined constituents, defined medias, or combinations thereof, such as RPMI, DMEM, etc. If desired an angiogenic compound such as VEGF can be included in the media to facilitate the formation of vascular cells or vasculature in the muscle tissue.

Figure 1:
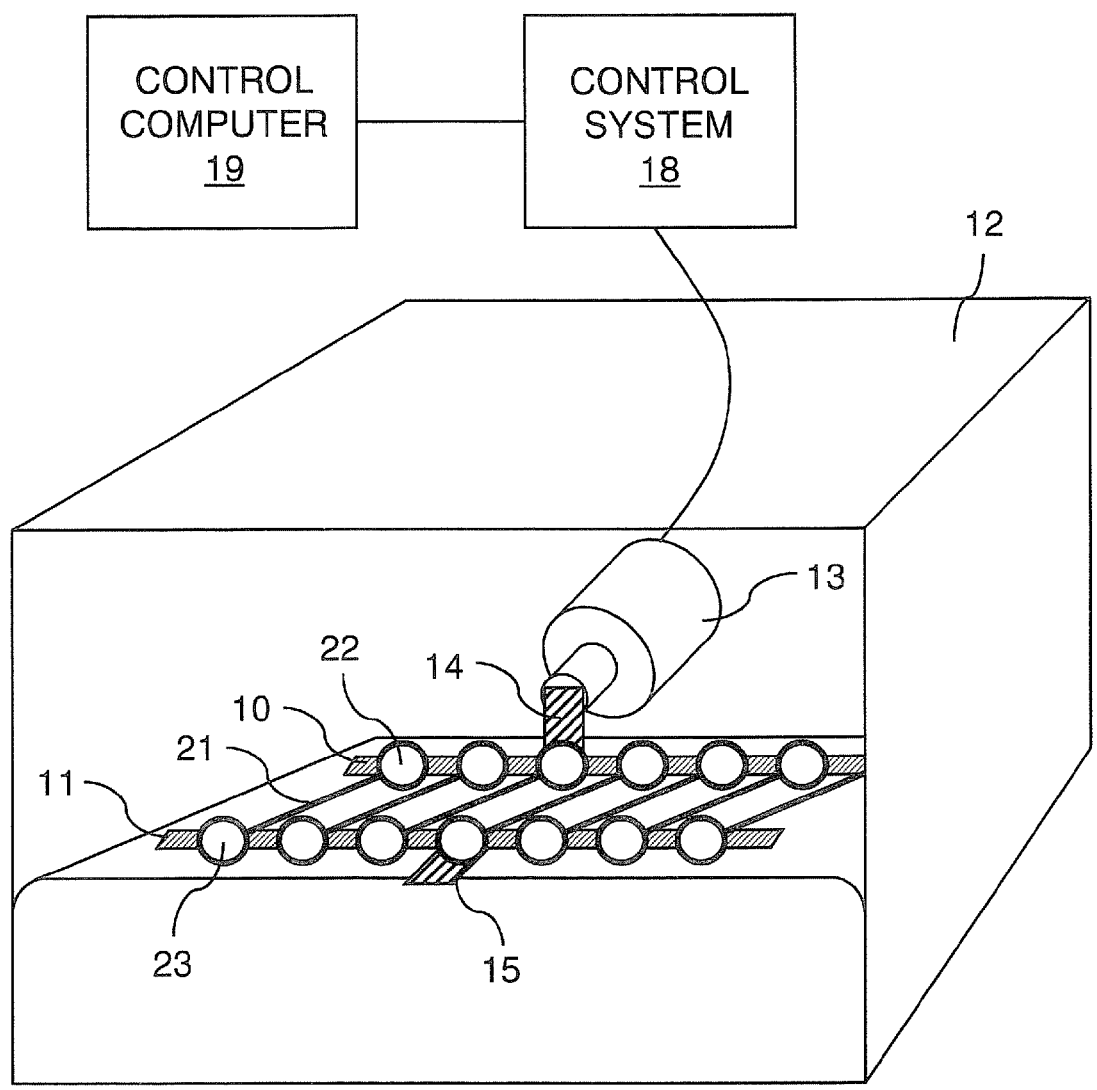
FIG. 1 is a schematic diagram of an apparatus of the present invention.

A device of the present invention is schematically illustrated in FIG. 1. The device comprises an actuator mounted on a tissue culture-compatible container and configured to provide controlled cyclic strain to attached scaffolds or other tissue constructs 21. These constructs are normally stretched in one direction. Constructs are supported between two holders or support engaging members 10 and 11, which can be formed from any structure for attaching a scaffold or developed tissue for tissue culture. The device has a removable lid, 12, which is a necessary component for setting up tissues for culturing and necessary to cover the box fully during culturing. The device has a single pass-through 13 consisting of a water-resistant bearing and mounting hardware. The device contains vertical adjustments both on the actuator connecting piece 14 (facilitated by a vertical slot and bolt, not shown) and on the pieces on the opposite side of the box 15 (also facilitated by vertical slot and bolt, not shown). The linear actuator stator (17) is controlled by a linear motor controller system (18) and a control computer (19), used for programming and subsequent monitoring of the actuator. The shaft (16) gives the motion to the support connecting piece 14, moving the horizontal piece 10 which provides the cyclic deformation to the constructs 21. The crosspieces 10, 11 can have any number of connecting points 22 for constructs. The connecting points are spaced so that each construct has its own volume immersed (fully or partially) in the culture medium within the apparatus.

While the device is shown with a single motor and actuator, it will be appreciated that an additional motor and engaging member may also be included to provide for elongation and relaxation along a second axis, if desired.

The apparatus may be used in a method of culturing organized skeletal muscle tissue from precursor muscle cells. As noted above, the method comprises: (a) providing precursor muscle cells on a support (e.g., a collagen support) in a tissue media; then (b) cyclically stretching and relaxing the support at least two or three times, up to 5, 10 or 20 times or more, along a first axis or direction of travel during a first time period. A preferred embodiment comprises (c) maintaining the support in a substantially static position during a second time period; and then (d) repeating steps (b) and (c) for a number of times sufficient to produce organized skeletal muscle tissue on the solid support from the precursor muscle cells.

If desired an angiogenic compound such as VEGF can be seeded on or carried by the solid support to facilitate the formation of vascular cells or vasculature in the muscle tissue.

The length of stretching of the solid support may be to a dimension at least 5% greater in length than the static position, and the relaxing may comprise retracting the support to a dimension not greater in length than the static position. In some embodiments the "static position" may be intermediate between the stretched and relaxed position, and in such cases the relaxing may comprise retracting the support to a dimension at least 5% lesser in length than the static position.

The first time period, during which the stretching and relaxing occurs, may be of any suitable length, for example from 2 or 3 minutes up to 10, 20 or 30 minutes in duration or more.

The second time period during which the support is maintained in a static position, may be of any suitable duration. In some embodiments the second time period is shorter than the first time period, and may be from 1 or 2 minutes in duration up to 10 or 20 minutes in duration. In other embodiments the second time period is longer than the first time period, and may be from 10 or 20 minutes in duration up to 40, 60 or 90 minutes in duration, or more. In some embodiments, such as where the first time period contains comparatively long intervals between stretching and relaxing, the need for a second time period may be obviated altogether.

In one preferred embodiment, the support is cyclically stretched and relaxed during a first "active" time period to a dimension of 10 percent greater and lesser in length than the static dimension at a rate of 3 cycles per minute for a total of five minutes, followed by a 55 minute "rest" second time period, continuously for 1 to 3 weeks of in vitro culture.

A particular advantage and application of the present invention is its ability to speed, accelerate or enhance the functional maturation or performance of muscle such as skeletal muscle grown in vitro (e.g., as exhibited by the ability of the muscle tissue to contract in response to contact to a 60 milliMolar KCl solution in vitro). Thus in some embodiments the total culturing time of the tissue, such as the repeating of steps (b) and (c) is carried out for a time of up to five days, or a time of up to one, two or three weeks, after which time a contractile response is preferably observed, with shorter culture times being preferred.

Skeletal muscle tissue produced as described herein may be used in vitro, in the apparatus described herein or in a separate apparatus, to examine the pharmacological or toxicological properties of compounds of interest (e.g., by adding the compound of interest to a culture medium in which the tissue is immersed, and examining the histological or mechanical properties of the tissue as compared to a control tissue).

Skeletal muscle tissue (with or without support) produced by the methods of the present invention is preferably "suturable" in that it has sufficient structural integrity to be surgically sutured or otherwise fastened at either end when implanted and thereafter develop tension upon contraction.

Skeletal muscle tissue produced as described herein may be used for the reconstruction of damaged tissue in a patient, e.g., a patient with a traumatic injury of an arm or leg. Such tissue may be utilized on the support (which is also implanted) or removed from the support and implanted into the subject. The skeletal muscle tissue may be implanted to "build" soft tissue (e.g., at the interface between an amputated limb and a prosthetic device) or to reconstruct (partially or totally) a damaged muscle (e.g., a muscle of the face, hand, foot, arm, leg, back or trunk). The cultured skeletal muscle tissue preferably has, in some embodiments, a size or volume of at least 1, 2, or 3 or more cubic centimeters (not counting the volume of the support if present), and/or a length of 1 cm to 50 cm, to provide sufficient tissue mass for implantation in a patient (e.g., in association with an existing muscle of the patient) and reconstruction of a skeletal muscle involved in, for example, movement of fingers.

For allogenic transplant into a patient, skeletal muscle as described herein may be matched or tissue-typed in accordance with known techniques, and/or the subject may be administered immune suppressive agents to combat tissue transplant rejection, also in accordance with known techniques.

The present invention is explained in greater detail in the following non-limiting Examples.

EXAMPLE 1

Figure 2:
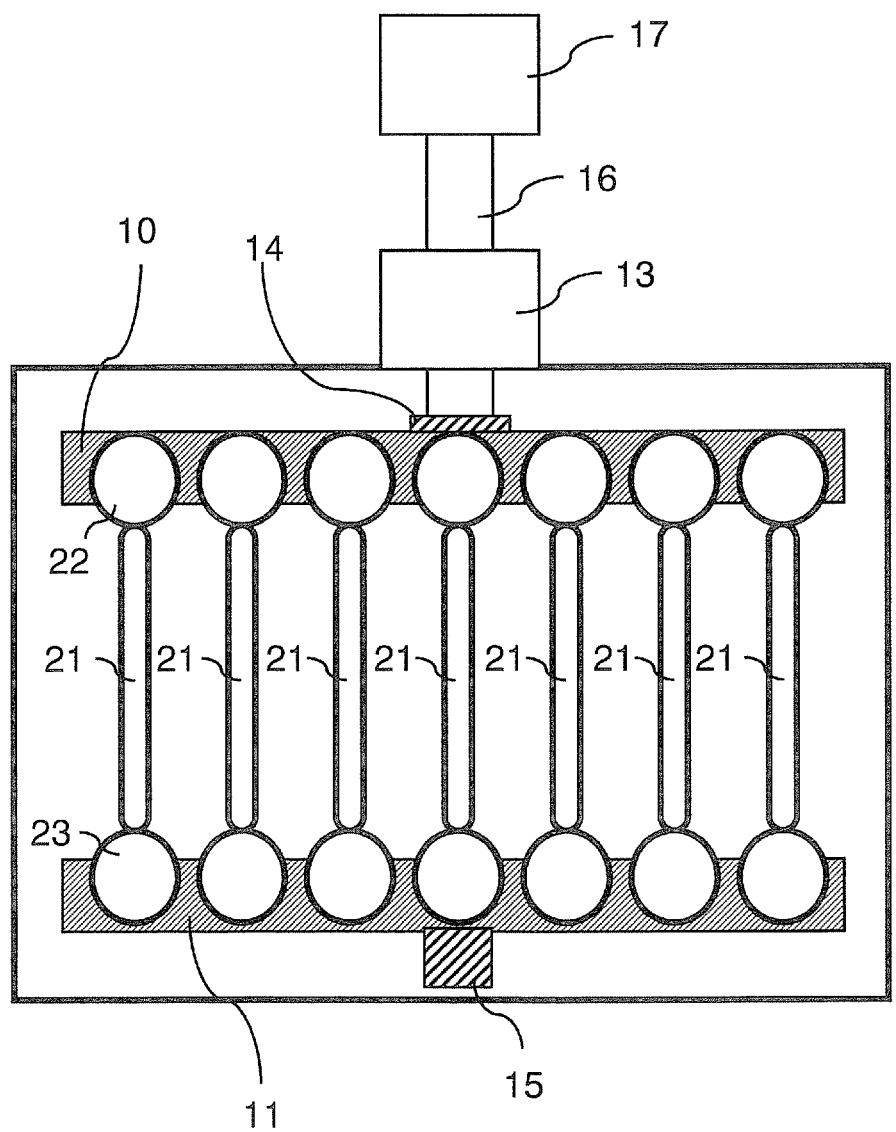
FIG. 2 is a top view of an apparatus of the present invention. The bioreactor engineered tissue is cyclically stretched by a linear motor that is, in turn, connected to a computer control system. There is great flexibility in the equipment and computer software for satisfying the desired biological boundary conditions.

A bioreactor system consisted of an actuator mounted on a tissue culture-compatible container which was designed to provide controlled cyclic strain to muscle tissue scaffolds, as shown in FIG. 2. The linear actuator was controlled by a linear motor controller system and a control computer, used for programming and subsequent monitoring of the actuator. Primary human skeletal muscle precursor cells were isolated, grown and expanded in culture. The cells were seeded onto collagen-based muscle scaffold strips derived from porcine bladder tissue ($1.0 \times 0.3 \times 0.3$ cm$^3$). After two days of static culture, the muscle cell seeded scaffolds were placed in the bioreactor system and programmed linear stretching cycles were applied (LinMot®). The controlled cycle strain was programmed to exert ±10% of the initial length of the cell seeded scaffolds at a frequency of 3 times per minute for the first 5 minutes of every hour. The bioreactor was continuously operated for up to 3 weeks after the initial set up. Muscle cell seeded scaffolds without cyclic stimulation served as controls. The muscle cell constructs were assessed for structural and functional parameters using scanning electron microscopy, histo- and immunohistochemistry, and physiologic tissue bath studies.

Figure 3A:
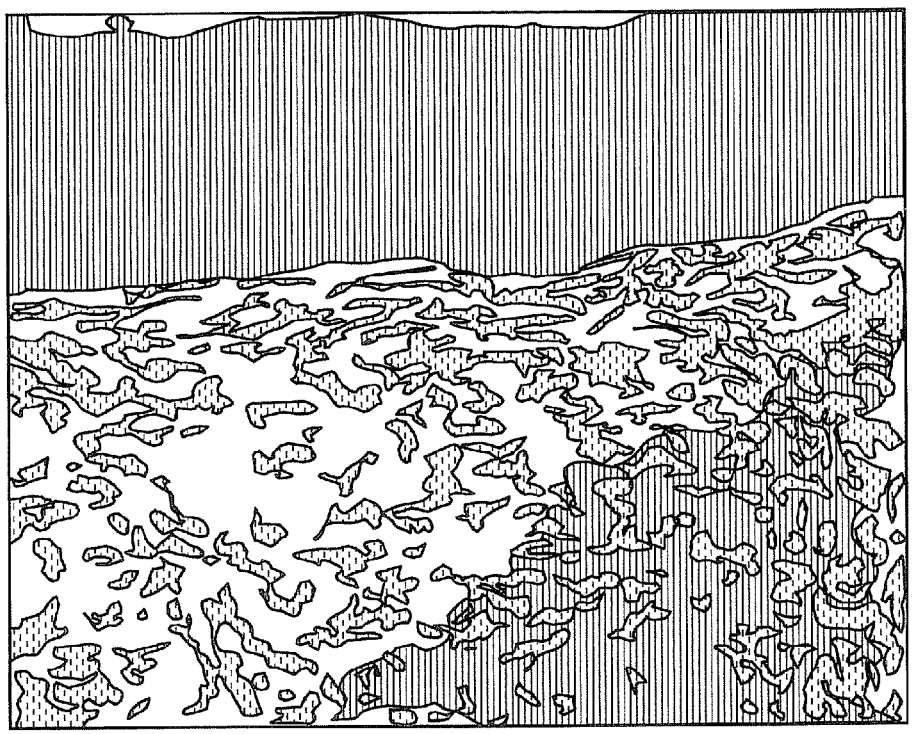
FIG. 3. H&E staining of bioengineered skeletal muscle following 5 days in the bioreactor. Note the dramatic change in orientation of the myocytes during static (A) growth versus culturing in the bioreactor (B). (C) Representative tracing of the contractile response of bioengineered muscle to KCl-induced depolarization in organ bath studies. A similar response was observed on two other strips. Myocytes seeded on a static scaffold in the same incubator for the same time period, exhibited no detectable contractile response to addition of KCl.
Figure 3B:
Figure 3C:
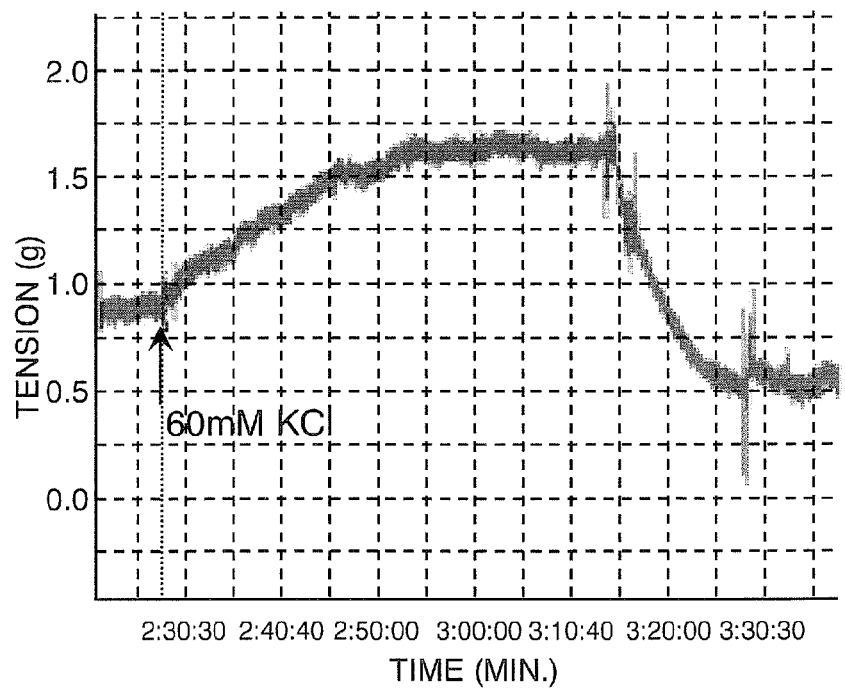

As shown in FIGS. 3A, 3B, and 3C, the bioreactor engineered muscle produced viable tissue with appropriate cellular organization. Scanning electron microscopy of the bioreactor stimulated muscle tissue showed a uniform attachment of muscle cells on the scaffold surface. Histologically, the bioreactor stimulated engineered muscle demonstrated unidirectional orientation by 5 days and continued to mature with time Presence of multinucleated myfibrils was evident within the tissue construct. The cells expressed muscle markers and produced extracellular matrices over time, as confirmed by immunohistochemistry and by Mason's Trichrome, respectively. The control scaffolds (myoblasts incubated under identical incubator conditions, but not in the bioreactor) showed disorganized muscle cells without any directional orientation. Physiologic organ bath studies of the bioreactor applied engineered muscle exhibited a reproducible contractile response to KCl-induced depolarization ($p<0.05$). The control scaffolds without the bioreactor stimulation failed to show any detectable contractile response.

This study demonstrates that an organized functional muscle tissue can be engineered using a unidirectional tissue bioreactor system. Muscle cell seeded scaffolds that are exposed to a constant cyclic biomechanical stimulation are able to achieve enhanced cellular organization and demonstrate significant contractile function. The use of this bioreactor system allowed for an enhanced cellular orientation and may accelerate muscle tissue formation for the bioengineering of clinically relevant sized muscle tissues.

EXAMPLE 2

This example presents the results of more detailed studies with the bioreactor system described above. The system, in overview, consisted of a linear actuator mounted on a tissue container to provide a controlled cyclic strain to muscle tissue scaffolds. Primary human muscle cells were seeded onto scaffolds and placed in the bioreactor system and subjected to cyclic strain equivalent to ≈±10% stretch of the original scaffold length; strain was applied 3 times/min for the first 5 min/hour for periods ranging from 5 days to 3 weeks. Following this conditioning protocol, the cell constructs were assessed for structural and functional parameters in vitro; cell and scaffold constructs under static culture conditions (i.e., no cyclic strain) were run in parallel. In a separate in vivo experiments, both the structures conditioned in the bioreactors for 5 days and control tissue structures maintained under static culture conditions were implanted onto the latissimus dorsi muscle of nude mice. At 3, 5, and 7 days after implantation, structures were retrieved and assessed for structural characteristics, while at 1, 2, 3 and 4 weeks, functional parameters were assessed.

Materials and Methods

Preparation of acellular tissue matrices. Acellular tissue matrices were prepared from porcine bladder as previously described (Ref). Briefly, excised porcine bladder tissues were placed in Triton X 1% (Sigma-Aldrich, Taufkirchen, Germany) for 24-48 h in the presence of 0.1% sodium azide, while agitated in a water bath at 37° C. The extraction of all cellular elements was confirmed histologically. Prepared acellular matrix was cut into the 1.5 cm×1.5 cm. Additional longitudinal incisions were created to increase the surface area for cell seeding and sutures were placed at both ends in order to secure the scaffold in the bioreactor. Scaffolds were sterilized by soaking them in Betadine solution for 1 day, and subsequently washed with 1% antibiotic PBC solution for 5 days before use in the these experiments.

Cell isolation, culture and characterisation. Primary human skeletal muscles cells were isolated by surgical biopsy from (i.e., psoas muscle) healthy volunteers ages 25-35 under the guidelines of Institutional Clinical Review Board of Wake Forest University Health Sciences School of Medicine. Muscles were washed 3-4 times with sterile PBS to remove debris before being cut into small pieces. Muscle tissues were plated onto 35 mm culture dishes with myogenic medium [340 mL low glucose DMEM (GIBCO Life Science, catalog no. CC-3161), 100 mL FBS (Fetal Bovine Serum), 50 mL HS (Horse Serum), 5 mL CEE (Chicken Embryo Extract) and 5 mL Penicillin/Streptomycin. When cells had achieved confluence they were further expanded on 150 mm culture dishes. Cells were passaged at confluence and always used before P10. Using this methodology we observed that $\approx$75-85% of the cells were desmin positive, confirming their myogenic phenotyped. P5 to P10 cells were transferred and seeded on the surfaces of acellular scaffold (with dimensions of $\approx$1.5 cm$^3$). The cell seeded scaffolds were then incubated in DMEM for 24 h.

Mechanical strain. A linear motor-driven stimulator device (Linmot, Va. Tech) was used for applying the mechanical stimulation, which consisted of cyclic unidirectional stretch and relaxation. The bioreactor system itself consisted of an actuator mounted on a tissue culture container in which the cell seeded scaffolds were secured. The linear actuator was, in turn, calibrated, controlled and programmed by a computer. To permit application of the cyclic stretch protocol, one end of the cell-seeded scaffold (i.e., tissue construct) was tied via sutures on a stationary bar, while the other end was secured to the movable bar that was attached to the linear motor and computer controller. As currently designed, the container can hold up to 10 tissue constructs at one time, with the maximal distance between the two bars of $\approx$10 cm. The media were changed every 3 days and tissue constructs were continuously provided with 95% air-5% $CO_2$, at 37° C. in an incubator.

Cyclic strain protocol. In this study, primary human skeletal muscle cells-seeded scaffolds were subjected to stretch and relaxation of $\approx$10% of their initial basal length. The exact protocol was as follows: tissue constructs were stretched 3 times/min (i.e., the entire stretch and relaxation protocol took 20 s) for the first 5 minutes of every hour for periods ranging from 5 days to 3 weeks. Muscle cell seeded scaffolds without cyclic stimulation were placed in the incubator on 150 mm culture dishes and served as controls.

Experimental Design for in vitro studies. Primary cultured myoblasts (600×10$^6$ cells/cm$^3$) were seeded onto the collagen-based scaffold (1.5×0.3×0.3 cm$^3$) derived from porcine bladder tissue. After 2 days of static culture, the cell-seeded scaffolds were placed in the bioreactor system described above. After periods ranging from 5 days to 3 weeks of mechanical stimulation, the muscle cell constructs were removed from the bioreactor system and assessed for structural and functional parameters. Again, muscle cell seeded scaffolds without cyclic stimulation served as controls.

Experimental Design for in vivo studies. Primary cultured myoblasts (600×10$^6$ cells/cm$^3$) were seeded onto the collagen-based scaffold (1.5×0.3×0.3 cm$^3$) derived from porcine bladder tissue (see Methods above). After 2 days of static culture, the cell-seeded scaffolds were moved into the bioreactor system. Following 1 week of mechanical stimulation, the muscle cell constructs and control tissue constructs without cyclic stimulation were implanted onto the lattissimus dorsi muscle of the nude mice). At 3, 5, and 7 days after implantation, the constructs were harvested and were assessed for structural and histological characteristics. At 1, 2, 3 and 4 weeks after implantation in vivo, the constructs were harvested and the contractility of the tissue constructs was assessed and evaluat to normal lattissimus dorsi muscle of the same nude mice.

Contractility Test. The KCl-induced contractile response was examined following 3 weeks of bioreactor conditioning in vitro. Contractility testing was also performed following 1 week of bioreactor preconditioning and then after 7, 14, 21 and 28 post-implantation in the latissimus dorsi of nude mide (5 tissue constructs/group). The contractile responses of the bioreactor-preconditioned muscle tissue was compared to that of statically seeded bioengineered tissue (i.e., 1 week of in vitro cell culture with no bioreactor preconditioning, as well as to the contractile responses observed in normal lattissimus dorsi muscle of similar dimensions that was harvested from the same nude mouse. The procedures for electrical field stimulation (i.e., EFS) followed previously published methods (5,6) with extensor digitorum longus (EDL) muscle (Radnoti Glass Technology Inc, Monrovia, Calif.).

After harvesting of the individual tissue constructs, the existing suture was used to attach the one end of the construct to a force transducer (Radnoti Model TRN001, Monrovia, Calif.) that was mounted on the spindle of a non-rotating micrometer head and then connected to an amplifier. The other end was attached to the glass hook at the bottom of the field-stimulating electrode (Radnoti model 160151). This configuration resulted in a vertically oriented muscle suspended between the two parallel platinum electrodes. The entire preparation was then submerged in a 25-mL organ chamber (Radnoti model 158326) filled with Krebs solution of the following composition: (pH 7.4; concentration in mM: 122.0 NaCl, 4.7 KCl, 1.2 MgCl$_2$, 2.5 CaCl$_2$, 15.4 NaHCO$_3$, 1.2 KH$_2$PO$_4$, and 5.5 glucose). The solution was aerated with a 95% O$_2$-5% CO$_2$ gaseous mixture and maintained at 37° C. with the help of a polystat circulator (Cole-Parner Instruments, Chicago, Ill.), and changed at 15-min intervals. After a 10-minute period of temperature equilibration, the optimal muscle length (i.e., Lmax) was determined by adjusting the stretch of the muscle through movement of the micrometer head. After determining the Lmax, isometric maximal twitch force was determined by gradually increasing voltage at 10 mV increments up to 100 mV, until maximal twitch force was achieved and recorded. Tetanic contractile force was then measured at frequencies of 40, 70, 100, and 120 Hz, with 1.5 s for each stimulation. The voltage used for tetanic testing was the same used to create maximal twitch force, with a duration of 2 ms and a delay of 2 ms. A 3-min rest period followed each stimulation. Electrical stimulation was provided by a neurostimulator (model S44B, Grass Instruments, Quincy, Mass.) and delivered to the constructs through platinum electrodes. Data were recorded and stored using a computerized data acquisition software (Mac Lab hardware and software; ADI Instruments, Natick, Mass.). At the conclusion of the contractile measurements, all muscles were weighed. All force measurements were observed on a digital display and recorded on a chart recorder.

Results: Compared to control structures under static culture conditions, structures derived from the bioreactor conditioning protocol (i.e., engineered tissue) produced viable muscle tissue with appropriate cellular organization. The engineered muscle showed unidirectional orientation within 5 days of bioreactor conditioning, and continued to mature with time. The presence of organized myofibrils was evident with the expression of muscle markers in the bioreactor stimulated structures. Extending the bioreactor conditioning period to 3 weeks produced a bioengineered tissue capable of generating a contractile response to depolarization with KCl. Finally, implantation of the engineered muscle tissue into the latissimus dorsi of nude mice following 3 days to 4 weeks of bioreactor conditioning yielded tissues with numerous structural and histological similarities to skeletal muscle, and 4 weeks after implantation the bioengineered muscle tissue showed a reproducible contractile response to EFS ($p<0.05$) that was approximately 30-50% of the response observed on comparably sized control segments from the same animal. No detectable contractile responses were observed on statically seeded constructs at any time point studied following implantation. In addition, in all cases, scaffolds maintained under static culture conditions showed disorganized tissue formation and multidirectional orientation of muscle cells both in vitro and in vivo.

Figure 4A:
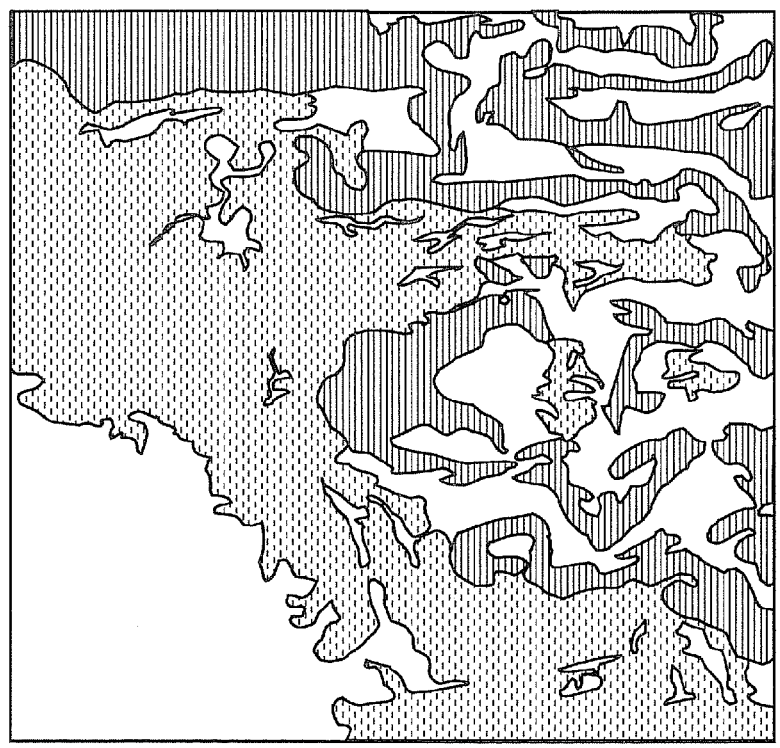
FIG. 4 shows staining of control skeletal muscle (A) and skeletal muscle cultured 7 days (B) in a bioreactor in accordance with methods of the present invention.
Figure 4B:
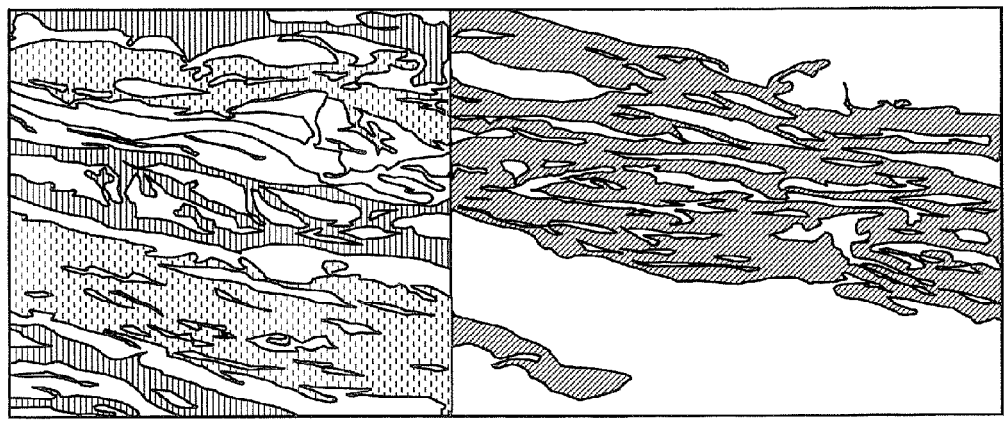

FIG. 4 shows staining of control skeletal muscle (A) and skeletal muscle cultured 7 days (B) in a bioreactor in accordance with methods of the present invention. Note the unidirectional orientation of cultured muscle (B) as compared to control muscle (A).

Figure 5A:
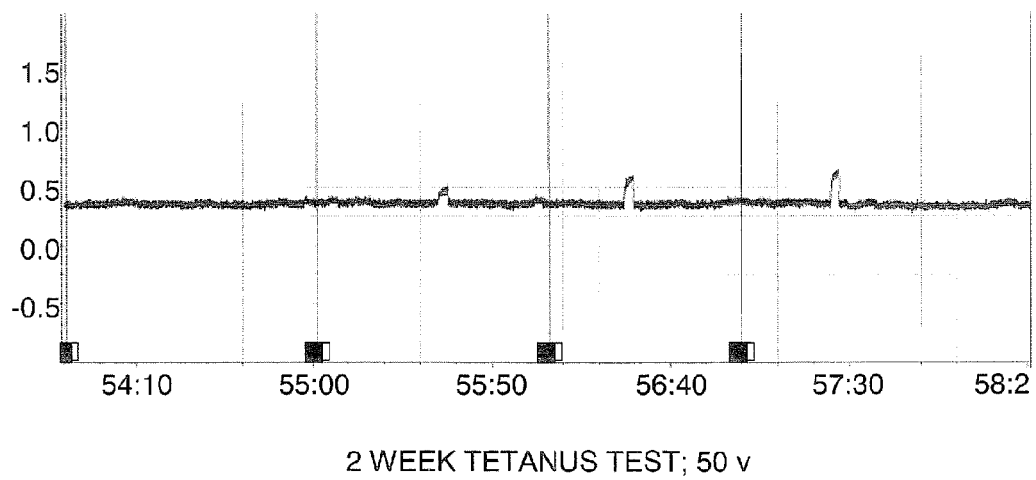
FIG. 5. Panels A & B provide representative examples of the contractile responses to electrical field stimulation (EFS) observed 2 and 4 weeks after implantation of bioengineered skeletal muscle on the latissimus dorsi of nu/nu mice.
Figure 5B:
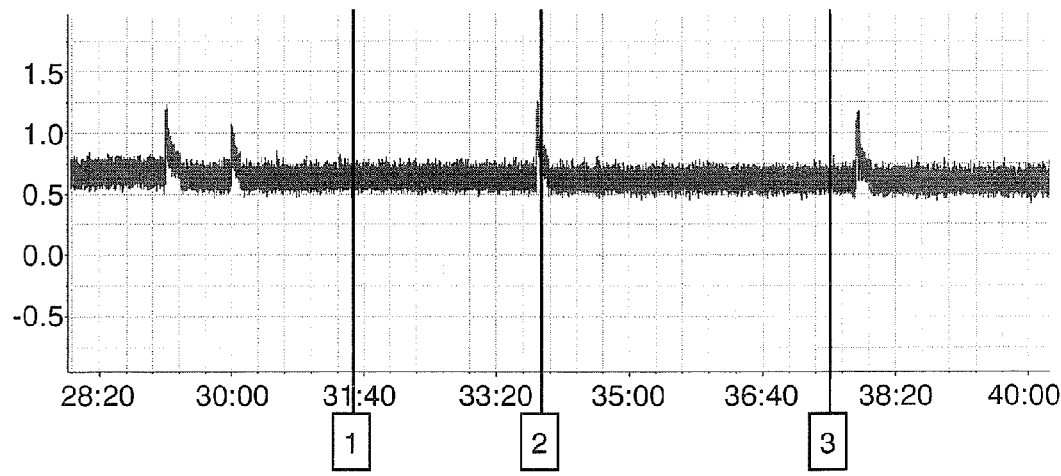
Figure 5C:
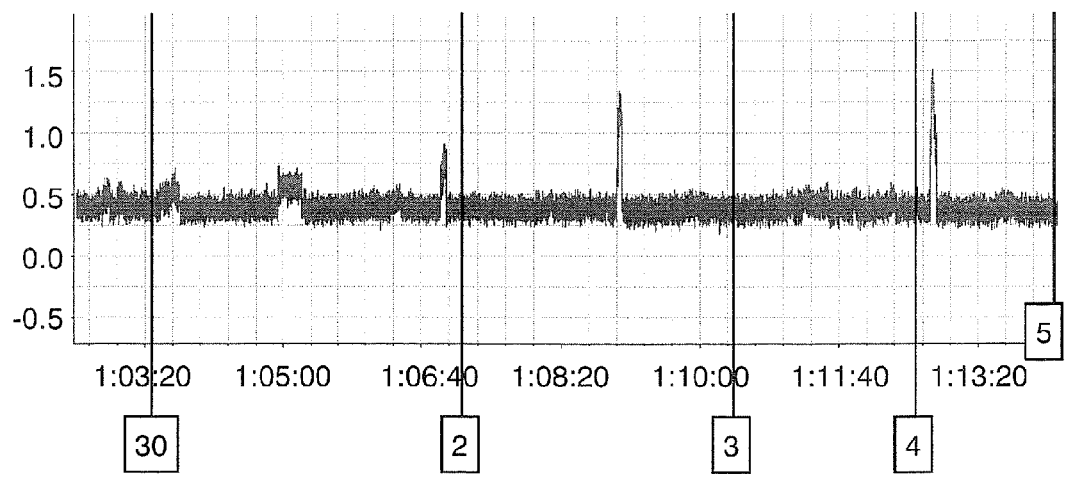

FIG. 5, panels A and B provide representative examples of the contractile responses to electrical field stimulation (EFS) observed 2 and 4 weeks after implantation of bioengineered skeletal muscle on the latissimus dorsi of nu/nu mice. Compare these responses with that observed in native latissimus dorsi muscle from an nu/nu mouse. Of major importance, only one month after implantation of bioengineered muscle, we observed 30-50% of the contractile response produced in native skeletal muscle.

FIG. 6 provides a graphical summary of the results of physiological experiments performed at the 4 week time point on isolate skeletal muscle tissue strips in vitro. Where: Normal denotes experimental results obtained with native skeletal muscle; Active denotes retrieved bioreactor preconditioned bioengineered skeletal muscle (i.e., active) 4 weeks after implantation on the latissimus dorsi; Control denotes experimental results obtained on bioengineered skeletal muscle that was NOT preconditioned in the bioreactor (cells+scaffold only and kept in an incubator under static conditions prior to implantation). See Methods for details. As illustrated, although the normal tissue produced greater contractile responses under all experimental conditions studied, the bioreactor preconditioned bioengineered skeletal muscle was able to generate contractile responses that ranged from ≈30-50% of normal muscle. In stark contrast, in the absence of bioreactor preconditioning (i.e., Control), no detectable contractile responses were observed at 4 weeks (or any other time point). Actual mean±SEM values can be found in the corresponding Table 1.

TABLE 1

Changes of Contractility at 50 V

|  | Normal | Active (4 weeks) | Control |
| --- | --- | --- | --- |
| No. Animal | 5 | 5 | 5 |
| 40 Hz | 4.09 ± 1.59 | 2.18 ± 0.98 | 0 |
| 70 Hz | 9.55 ± 2.04 | 2.78 ± 1.12 | 0 |
| 100 Hz | 15.49 ± 4.25 | 4.66 ± 1.37 | 0 |
| 120 Hz | 16.8 ± 4.09 | 5.40 ± 1.52 | 0 |
| Max twitch | 9.16 ± 2.12 (100 V) | 3.46 ± 1.05 (90 V) | 0 |

Data are expressed as Mean and SD.

FIG. 7 provides a graphical summary of the results of all physiological experiments performed on isolate skeletal muscle tissue strips in vitro. As illustrated, within 2 weeks after implantation, bioreactor preconditioned bioengineered skeletal muscle strips are capable of generating measurable contractile responses. Again, while the bioengineered skeletal muscle generated significantly less tension than native latissimus dorsi at all time points thus far studied, these are the first data that we are aware of which document force generation of this magnitude in bioengineered human skeletal muscle. Actual mean±SEM values can be found in the corresponding Table 2.

TABLE 2

Time-dependent changes in contractility of bioreactor-conditioned engineered muscle tissue

|  | Normal | 1 wk. | 2 wks. | 3 wks. | 4 wks. |
| --- | --- | --- | --- | --- | --- |
| No. Animal | 5 | 5 | 5 | 5 | 5 |
| 40 Hz | 4.09 ± 1.59 | 0 | 0.32 ± 0.13 | 0.19 ± 0.1 | 2.18 ± 1.31 |
| 70 Hz | 9.55 ± 2.04 | 0 | 0.67 ± 0.63 | 1.73 ± 0.72 | 2.78 ± 1.12 |
| 100 Hz | 15.49 ± 4.25 | 0 | 1.75 ± 1.31 | 4.21 ± 1.70 | 4.66 ± 1.47 |
| 120 Hz | 16.8 ± 4.09 | 0 | 2.83 ± 1.42 | 3.64 ± 1.89 | 5.40 ± 1.53 |

Data are expressed as Mean and SD.
There was no contractile response in all control (cells, but not bioreactor conditioning) constructs of 1 wk, 2 wks, 3 wks and 4 wks.

Conclusion: This study demonstrates that organized functional muscle can be engineered using a computerized bioreactor system on a biodegradable scaffold (matrix). That is, following isolation and expansion, muscle cell seeded scaffolds that are exposed to a cyclic stimulation protocol are able to achieve enhanced cellular organization and accelerated tissue formation/maturation both in vitro and in vivo, with significant contractile function in all cases. The use of this bioreactor system may accelerate muscle formation for reconstructive or replacement surgery in patients with localized functional skeletal muscle deficits.

REFERENCES

1. Vandenburgh, Mechanical forces and their second messengers in stimulating cell growth in vitro. Am J. Physiol. 1992 March; 262(3 Pt 2):R350-5.
2. Mechanical stimulation of skeletal muscle generates lipid-related second messengers by phospholipase activation. J Cell Physiol. 1993 April; 155(1):63-71.
3. Dennis R G, Kosnik P E. Excitability and isometric contractile properties of mammalian skeletal muscle constructs engineered in vitro. In Vitro Cell and Dev Biol Animal. 36:327-335, 2000]
4. Huang Y, Dennis R G, Larkin L, Baar K. Rapid formation of functional muscle in vitro using fibrin gels. J Appl Physiol 98: 706-713, 2005.
5. Bolognesis M P, Chen L E, Seaber A V, Urbaniak J R. Protective effect of hypothermia on contractile force in skeletal muscle. J Orthop Res 1996: 14; 390-395.
6. Chen L E, Seaber A V, Nasser R M, Stamler J S, Urbaniak J R. Effects of S-nitroso-N-acetylcysteine on contractile function of reperfused skeletal muscle. Am J Physiol 1998; 274: 822-829.
7. Stewart D M. The role of tension in muscle growth-Organ and Tissue Growth. New York: Associated Press, 1972, p. 77-100.
8. Vandenburgh H H. Motion into mass: how does tension stimulate muscle growth. Med Sci Sports Exerc 19: S142:S149, 1987.]
9. Vandenburgh H H, Karlisch P. 1989. Longitudinal growth of skeletal myotubes in vitro in a new horizontal mechanical cell stimulator. In Vitro Cell Dev Biol 25:607-616.
10. Cheema U, Yang S Y, Mudera V, Goldspink G, Brown R A. 2003. 3-D in vitro model of early skeletal muscle development. Cell Motil Cytoskeleton 54:226-236.)
11. Alberts B, Johnson A, Lewis J, Raff M, Roberts K, Walter P. Histology: The Lives and Deaths of Cells in Tissues. Molecular Biology of The Cell (4$^{th}$ Ed). New York: Garland Science, 2002, p. 1259-1312.
12. Dennis R G, Kosnick P E, Gilbert M E, Faulkner J A. Excitability and contractility of skeletal muscle engineered from primary cultures and cell lines. Am J Physiol Cell Physiol 280:C288-C295, 2001.
13. Goldspink G, Scutt A, Loughna P T, Wells D J, Jaenicke T, Gerlach G F. 1992. Gene expression in skeletal muscle in response to stretch and force generation. Am J Physiol 262:R356-R363.)
14. Grinnell F. 2003. Fibroblast biology in three-dimensional collagen matrices. Trends Cell Biol 13(5):264-269.
15. Graf R, Freyburg M, Kaiser D, Friedl P. 2002. Mechanosensitive induction of apoptosis in fibroblasts is regulated by thrombospondin-1 and integrin associated protein (CD47). Apoptosis 7:493-498.
16. Tian B, Lessan K, Kahm J, Kleidon J, Henke C. 2002. Beta 1 integrin regulates fibroblast viability during collagen matrix contraction through a phosphatidylinositol 3-kinase/AKT/protein kinase B signalling pathway. J Biol Chem 277:24667-24675.
17. Hantai D, Tassin A M, Gautron J, Labat-Robert J. Biosynthesis of laminin and fibronectin by rat satellite cells during myogenesis in vitro. Cell 9:647-654, 1985.

The foregoing is illustrative of the present invention, and is not to be construed as limiting thereof. The invention is defined by the following claims, with equivalents of the claims to be included therein.

That which is claimed is:

1. Cultured organized skeletal muscle tissue produced by a process comprising:
    (a) providing a decellularized tissue support in a tissue media in a bioreactor, said support comprising precursor muscle cells; then
    (b) cyclically stretching and relaxing said support at least twice along a first axis during a first time period; and then
    (c) maintaining said support in a substantially static position during a second time period; and then
    (d) repeating steps (b) and (c) for a number of times sufficient to produce said cultured organized skeletal muscle tissue on said support from said precursor muscle cells, wherein repeating steps (b) and (c) is carried out for a time of up to two weeks and results in the cultured organized skeletal muscle tissue having unidirectional orientation, and
    wherein said cultured organized skeletal muscle tissue is further characterized by enhancing cellular organization, contractile function and tissue formation when implanted in vivo.

2. The cultured organized skeletal muscle tissue of claim 1, wherein said cyclically stretching and relaxing is carried out at least three times during said first time period.

3. The cultured organized skeletal muscle tissue of claim 1, wherein said stretching comprises extending said support to a dimension at least 5% greater in length than said static position.

4. The cultured organized skeletal muscle tissue of claim 1, wherein said first time period is from 2 to 30 minutes in duration.

5. The cultured organized skeletal muscle tissue of claim 1, wherein said second time period is from 10 to 100 minutes in duration.

6. The cultured organized skeletal muscle tissue of claim 1, wherein said repeating of steps (b) and (c) is carried out for a time of five days to one week.

7. The cultured organized skeletal muscle tissue of claim 1, wherein said precursor muscle cells are human cells.

8. The cultured organized skeletal muscle tissue of claim 1, wherein said cultured organized skeletal muscle tissue is suturable and is 1 to 50 cm in length.

9. The cultured organized skeletal muscle tissue of claim 1, wherein said cultured organized skeletal muscle tissue contracts in response to electrical stimulation four weeks after in vivo implantation.

10. The cultured organized skeletal muscle tissue of claim 1, wherein said decellularized tissue support comprises decellularized smooth muscle or decellularized skeletal muscle.

11. The cultured organized skeletal muscle tissue of claim 10, wherein said decellularized tissue support comprises decellularized mammalian bladder.

12. An implantable skeletal muscle construct produced by a process comprising:
    (a) providing a suturable support in a tissue media in a bioreactor, wherein said suturable support comprises mammalian precursor muscle cells, and wherein said suturable support comprises decellularized smooth muscle or decellularized skeletal muscle; then (b) cyclically stretching and relaxing said suturable support at least twice along a first axis during a time period of from 2 to 30 minutes in duration; and then (c) maintaining said suturable support in a substantially static position for a time period of from 10 to 100 minutes in duration; and then (d) repeating steps (b) and (c) for a number of times sufficient to produce said implantable skeletal muscle construct on said suturable support from said precursor muscle cells, wherein repeating steps (b) and (c) is carried out for a time of up to two weeks and results in the implantable skeletal muscle construct having unidirectional orientation, and wherein said implantable skeletal muscle construct is further characterized by enhancing cellular organization, contractile function and tissue formation when implanted in vivo.

13. The implantable skeletal muscle construct of claim 12, wherein said suturable support comprises decellularized mammalian bladder.

14. The implantable skeletal muscle construct of claim 12, wherein said suturable support comprises decellularized porcine bladder.

15. The implantable skeletal muscle construct of claim 12, wherein said precursor muscle cells are human cells.

* * * * *